US007390491B2

(12) United States Patent
Takada et al.

(10) Patent No.: US 7,390,491 B2
(45) Date of Patent: Jun. 24, 2008

(54) AGENTS COMPRISING MIDKINE OR AN INHIBITOR THEREOF AS ACTIVE INGREDIENT

(75) Inventors: Tohru Takada, Aichi (JP); Kazuhiro Toriyama, Aichi (JP); Hisako Muramatsu, Aichi (JP); Takashi Muramatsu, Aichi (JP)

(73) Assignee: Takashi Muramatsu (JP)

(*) Notice: Subject to any disclaimer, the term of this patent is extended or adjusted under 35 U.S.C. 154(b) by 564 days.

(21) Appl. No.: 10/298,889

(22) Filed: Nov. 18, 2002

(65) Prior Publication Data

US 2003/0072739 A1 Apr. 17, 2003

Related U.S. Application Data

(62) Division of application No. 09/462,725, filed as application No. PCT/JP98/03161 on Jul. 14, 1998, now abandoned.

(30) Foreign Application Priority Data

| Jul. 14, 1997 | (JP) | ................................. 9/205320 |
| Jul. 14, 1997 | (JP) | ................................. 9/205332 |

(51) Int. Cl.
    *A61K 39/395* (2006.01)
    *C07K 16/22* (2006.01)
    *C07K 16/46* (2006.01)

(52) U.S. Cl. ............... 424/145.1; 424/133.1; 424/141.1; 424/142.1; 424/158.1; 530/387.3; 530/388.1; 530/388.15; 530/388.23; 530/389.1; 530/389.2

(58) Field of Classification Search ....................... None
See application file for complete search history.

(56) References Cited

U.S. PATENT DOCUMENTS

| 5,206,223 | A | 4/1993 | Vlodavsky et al. |
| 5,210,026 | A | 5/1993 | Kovesdi et al. |
| 5,474,987 | A | 12/1995 | Cohen et al. |
| 5,629,284 | A | 5/1997 | Kazuhiko et al. |
| 6,083,907 | A | 7/2000 | Uchida et al. |
| 6,383,480 | B1 | 5/2002 | Kikuchi et al. |

FOREIGN PATENT DOCUMENTS

| EP | 583360 | 11/1992 |
| EP | 0 535 336 A2 | 4/1993 |
| EP | 0 569 703 A2 | 11/1993 |
| EP | 754460 | 1/1997 |
| EP | 251134 | 1/1998 |
| EP | 0 937 461 A1 | 8/1999 |
| JP | 6388127 | 4/1988 |
| JP | 6507635 | 9/1994 |
| JP | 8277224 | 10/1996 |
| WO | WO 92/19249 | 11/1994 |
| WO | WO 94/28889 | 12/1994 |
| WO | WO 96/24362 | 1/1997 |
| WO | WO 98/01151 | 1/1998 |

OTHER PUBLICATIONS

Imiela et al. Oral heparin in the treatment of rheumatoid arthritis. Arch Immunol Ther Exp (Warsz). 1995;43(5-6):313-5.*
Brandt, K.D. "Management of Osteoarthritis." Chapter 80 in: Kelley, W. N., Textbook of Rheumatology (Philadelphia, Saunders, 1993), pp. 1389-1390.*
Nelson et al. Heparin oligosaccharides bind L- and P-selectin and inhibit acute inflammation. Blood. Dec. 1, 1993;82(11):3253-8.*
Kodelja, V. et al. "Differences in Angiogenic Potential of Classically vs Alternatively Activated Macrophages" *Immunobiol.*, Nov. 1997, pp. 478-493, vol. 197, No. 5.
Hiramatsu, K. et al., "Midkine Induces Histamine Release from Mast Cells and the Immediate Cutaneous Response" *Biochemistry and Molecular Biology International.*, 1998, pp. 453-462, vol. 44, No. 3.
Sun, X. et al. "Midkine, A New Heparin-Binding Growth/Differentiation Factor: Expression and Distribution during Embryogenesis and Pathological Status" *Cong. Anom.*, 1998, pp. 25-38, vol. 38.
Takada, T. et al. "Midkine, a Retinoic Acid-Inducible Heparin-Binding Cytokine in Inflammatory Responses: Chemotactic Activity to Neutrophils and Association with Inflammatory Synovitis" *J. Biochem*, 1997, pp. 453-458, vol. 122.
Takada, T. et al. "Midkine, a Retinoic Acid-Inducible Heparin-Binding Cytokine, Is a Novel Regulator of Intracellular Calcium in Human Neutrophils" *Biochemical and Biophysical Research Communications*, 1997, pp. 756-761, vol. 241.
Bowie, J. U. et al. "Deciphering the Message in Protein Sequences: Tolerance to Amino Acid Substitutes" *Science*, 1990, pp. 1306-1310, vol. 247.
Ngo, J. T. et al. "Computational Complexity, Protein Structure Prediction, and the Levinthal Paradox" In: *The Protein Folding Problem and Tertiary Structure Prediction*, 1994, pp. 433 and 492-495, Merz and LeGrand (eds), Springer Verlag.
Lodish, H. et al. "Noncovalent Bonds and the Structures of Biological Molecules" In: *Molecular Cell Biology, Third Edition*, 1995, p. 23, W. H. Freeman and Company, New York.
Muramatsu, H. et al. "Purification of Recombinant Midkine and Examination of its Biological Activites: Functional Comparison of New Heparin Binding Factors" *Biochemical and Biophysical Research Communications*, 1991, pp. 652-658, vol. 177, No. 2.
Michikawa, M. et al. "Retinoic Acid Responsive Gene Product, Midkine, Has Neurotrophic Functions for Mouse Spinal Cord and Dorsal Root Ganglion Neurons in Culture" *Journal of Neuroscience Research*, 1993, pp. 530-539, vol. 35.
Muramatsu, H. et al. "Midkine, A Retinoic Acid-Inducible Growth/Differentiation Factor: Immunochemical Evidence for the Function and Distribution" *Developmental Biology*, 1993, pp. 392-402, vol. 159.
Kadomatsu, K. et al. "A Retinoic Acid Responsive Gene *MK* Found in the Teratocarcinoma System Is Expressed in Spatially and Temporally Controlled Manner during Mouse Embryogenesis" *The Journal of Cell Biology*, 1990, pp. 607-616, vol. 110.

(Continued)

*Primary Examiner*—David S Romeo
(74) *Attorney, Agent, or Firm*—Saliwanchik, Lloyd & Saliwanchik (57) ABSTRACT

Midkine (MK), which is a retinoic acid-inducible heparin-binding growth factor, enhances neutrophilic migration and exists in an inflammatory state at a high concentration. The midkine or its inhibitors can be used for treating neutrophilic functional disorders or inflammatory diseases.

15 Claims, 6 Drawing Sheets

OTHER PUBLICATIONS

Mitsaidis, T. A. et al. "Expression of the heparin-binding cytokines, midkine (MK) and HB-GAM (pleiotrophin) is associated with epithelial-mesenchymal interactions during fetal development and organogenesis" *Development*, 1995, pp. 37-51, vol. 127.

Mitsiadis, T. A. et al. "Midkine (MK), a Heparin-binding Growth/Differentiation Factor, Is Regulated by Retinoic Acid and Epithelial-Mesenchymal Interactions in the Developing Mouse Tooth, and Affects Cell Proliferation and Morphogenesis" *The Journal of Cell Biology*, 1995, pp. 267-281, vol. 129, No. 1.

Tsutsui, J-I. et al. "A New Family of Heparin-binding Growth/Differentiation Factors: Increased Midkine Expression in Wilms' Tumor and Other Human Carcinomas" *Cancer Research*, 1993, pp. 1281-1285, vol. 53.

Aridome, K. et al. "Increased Midkine Gene Expression in Human Gastrointestinal Cancers" *Jpn. J. Cancer Res.*, 1995, pp. 655-661, vol. 86.

Garver, R. I. et al. "Midkine and Pleiotrophin Expression in Normal and Malignant Breast Tissue" *Cancer*, 1994, pp. 1584-1590, vol. 74, No. 5.

Nakagawara, A. et al. "Differential Expression of Pleiotrophin and Midkine in Advanced Neuroblastomas" *Cancer Research*, 1995, pp. 1792-1797, vol. 55.

Yasuhara, O. et al. "Midkine, A Novel Neurotrophic Factor, Is Present In Senile Plaques of Alzheimer Disease" *Biochemical and Biophysical Research Communications*, 1993, pp. 246-251, vol. 192, No. 1.

Yoshida, Y. et al. "Midkine is present in the early stage of cerebral infarct" *Developmental Brain Research*, 1995, pp. 25-30, vol. 85.

Kojima, S. et al. "Midkine Enhances Fibrinolytic Activity of Bovine Endothelial Cells" *The Journal of Biological Chemistry*, 1995, pp. 9590-9596, vol. 270, No. 16.

Springer, T. A. "Traffic Signals for Lymphocyte Recirculation and Leukocyte Emigration: The Multistep Paradigm" *Cell*, 1994, pp. 301-314, vol. 76.

Kadomatsu, K. et al. "cDNA Cloning and Sequencing of a New Gene Intensely Expressed in Early Differentiation Stages of Embryonal Carcinoma Cells and in Mid-Gestation Period of Mouse Embryogenesis" *Biochemical and Biophysical Research Communications*, 1988, pp. 1312-1318, vol. 151, No. 3.

Kaneda, N. et al. "Midkine, a Heparin-Binding Growth/Differentiation Factor, Exhibits Nerve Cell Adhesion and Guidance Activity for Neurine Outgrowth In Vitro" *J. Biochem.*, pp. 1150-1156, No. 119.

Kojima, T. et al. "Human Ryudocan from Endothelium-like Cells Binds Basic Fibroblast Growth Factor, Midkine, and Tissue Factor Pathway Inhibitor" *The Journal of Biological Chemistry*, 1996, pp. 5914-5920, vol. 271, No. 10.

Roguska, M. A. et al. "Humanization of murine monoclonal antibodies through variable domain resurfacing" *Proc. Natl. Acad. Sci USA*, 1994, pp. 969-973, vol. 91.

Winter, G. et al. "Making Antibodies by Phage Display Technology" *Annu. Rev. Immunol.*, 1994, pp. 433-455, vol. 12.

Lonberg, N. et al. "Antigen-specific human antibodies from mice comprising four distinct genetic modifications" *Nature*, 1994, pp. 856-859, vol. 368.

Muramatsu, H. et al. "Enzyme-Linked Immunoassay for Midkine, and Its Application to Evaluation of Midkine Levels in Developing Mouse Brain and Sera from Patients with Hepatocellular Carcinomas" *J. Biochem.*, 1996, pp. 1171-1175, vol. 119.

Elenius, K. et al. "Induced Expression of Syndecan in Healing Wounds" *The Journal of Cell Biology*, 1991, pp. 585-595, vol. 114, No. 3.

* cited by examiner

|  | | MK concentration (ng/ml) in top chamber | | | |
|---|---|---|---|---|---|
|  | | 0 | 1 | 10 | 100 |
| MK concentration (ng/ml) in bottom chamber | 0 | 3.2±0.5 | 2.1±0.4 | 3.7±0.5 | 2.8±0.3 |
| | 1 | 5.7±0.6 | 2.6±0.6 | 4.5±0.7 | 3.5±0.4 |
| | 10 | 8.3±1.2 | 5.5±0.7 | 4.7±0.5 | 2.6±0.4 |
| | 100 | 6.8±0.5 | 6.9±0.6 | 6.9±0.7 | 5.8±0.9 |

Figure 6

AGENTS COMPRISING MIDKINE OR AN INHIBITOR THEREOF AS ACTIVE INGREDIENT

This application is a division of U.S. application Ser. No. 09/462,725, filed May 1, 2000, now abandoned, which is the national stage of international application No. PCT/JP98/03161, filed Jul. 14, 1998.

TECHNICAL FIELD

The present invention relates to agents for controlling neutrophilic functions containing midkine or its inhibitor as an active ingredient. The agents can be utilized for treating diseases associated with neutrophils such as neutrophilic functional disorders or inflammatory diseases.

BACKGROUND ART

Neutrophils, which is a type of granulocytes, have migratory, phagocytic, and microbicidal activities, and play important roles in biological protection against infectious agents such as bacteria or fungi. There are some diseases associated with neutrophils.

Neutrophilic functional disorders, in which one or more of the above-mentioned biological activities of neutrophils are impaired, include, for example, lazy-leukocyte (chemotaxis-deficient leukocyte) syndrome, one of the neurotaxis deficient diseases. In patients affected with this syndrome, neutrophils are markedly decreased in number in the peripheral blood, and their migratory activity is impaired, although they are present at a normal level in the bone marrow. Patients suffering from neutrophilic functional disorders are very few, and drugs applicable to the disorders are so far not commercially available.

Another example of the diseases associated with neutrophils is inflammatory diseases. Inflammatory reaction is a biological protection to tissue damages caused by inflammatory stimulation (e.g., foreign bodies such as bacteria or others, and physicochemical stimulation, etc.). The inflammatory reaction basically removes harmful stimulation from the living body and restores local tissue structures and functions. The activated inflammatory system is, however, toxic to normal tissues and cells, and the strongly expressed inflammatory reaction should be suppressed.

The inflammatory reaction includes three major processes; 1) increment of blood supply to infected sites; 2) enhancement of vascular permeability due to the reaction in vascular endothelial cells; and 3) mobilization of leukocytes, specifically, neutrophils and some macrophages, from capillaries to tissues, and subsequent migration to infected sites. These processes result in accumulation and infiltration of neutrophils as well as macrophages at their target sites. Thus repressing the neutrophilic functions has been believed to be effective for controlling the inflammatory reaction.

Various anti-inflammatory drugs have been developed. They are categorized into two groups, non-specific anti-inflammatory drugs (steroidal anti-inflammatory drugs and non-steroidal anti-inflammatory drugs) and specific anti-inflammatory drugs (anti-rheumatic drugs, anti-podagric drugs, immunosuppressants, etc.). Analgesic and anti-inflammatory drugs (non-steroidal anti-inflammatory drugs, NSAIDs) are used mainly, and anti-rheumatic drugs (disease-modifying anti-rheumatic drugs, DMARDs) and steroidal drugs are used secondarily, in chemotherapy for rheumatoid arthritis (RA). However, NSAIDs cause acute gastric mucosal lesions (AGML), and are thus often used in the form of prodrugs to avoid AGML.

Recently, midkine (MK) has been identified as a heparin-binding polypeptide with the molecular weight of 13 kDa and a retinoic acid-inducible gene product. Reported midkine functions include maintaining and differentiating embryonic nerve cells and enhancing neurite extension; promoting division of specific cell lines (Muramatsu, H. et al., Biochem. Biophys. Res. Commun. 177: 652-658, 1991; and Michikawa, M. et al., J. Neurosci. Res. 35: 530-539, 1993; Muramatsu, H. et al., Dev. Biol. 159: 392-402, 1993); regulating embryonic development (Kadomatsu, K. et al., J. Cell. Biol. 110: 607-616, 1990; Mitsiadis, T. A. et al., Development 121: 37-51, 1995); etc. Furthermore, anti-midkine antibody reportedly inhibits dentition in vitro (Mitsiadis, T. A. et al, J. Cell. Biol. 129: 267-281, 1995).

It has been revealed that midkine plays crucial roles in restoration of damaged tissues and some diseases. The expression patterns of midkine were investigated in various human carcinomas. The studies revealed that midkine expression is elevated in various cancers including stomach cancer, colon cancer, pancreatic cancer, lung cancer, thoracic cancer, and liver cancer (Tsutsui, J. et al., Cancer Res. 53: 1281-1285, 1993; Aridome, K. et al., Jap. J. Cancer Res. 86: 655-661, 1995; and Garver, R. I. et al., Cancer 74: 1584-1590, 1994). The high-level expression of midkine correlates with unfavorable prognoses in patients affected with neuroblastoma (Nakagawara, A. et al., Cancer Res. 55: 1792-1797, 1995). Midkine accumulates in senile plaques of most patients with Altzheimer's disease (Yasuhara, O. et al. Biochem. Biophys. Res. Commun. 192: 246-251, 1993). Midkine is expressed in regions with edema at early stages of cerebral infarction (Yoshida, Y. et al., Dev. Brain Res. 85: 25-30, 1995). These findings indicate that midkine may be associated with restoration of damaged tissues and tissue abnormalities that are signs of some diseases.

DISCLOSURE OF THE INVENTION

An objective of the present invention is to provide novel agents for controlling neutrophilic functions, specifically, for treating neutrophilic functional disorders, for enhancing chemotaxis and haptotaxis of neutrophils, and treating inflammatory diseases.

A recent report (Kojima, S. et al., J. Biol. Chem. 270: 9590-9596, 1995) has shown that midkine enhances the activity of plasminogen activator in vascular endothelial cells and also enhances the fibrinolytic activity that is important in the migration of cells to inflammatory sites and in cell migration in cancer cell infiltration and angiogenesis. It has also been clarified that midkine triggers leukocyte mobilization at the initial stage of inflammation (Timothy, A. S. Cell 76:301-314, 1994). Based on these reports, the present inventors analyzed the expression of midkine in inflammation models associated with rheumatoid arthritis (RA) and osteoarthritis (OA). The results indicate that the level of midkine was elevated in the inflammatory states closely associated with neutrophils. The present inventors also examined effect of midkine on neutrophilic migration and found that a matrix-bound midkine stimulates neutrophilic migration.

Furthermore, based on the findings of the close relationship between midkine and neurotaxis as well as between midkine and inflammation, the present inventors have found that the diseases associated with neutrophilic functions, including, for example, neutrophilic functional disorders and inflammatory diseases, can be treated by controlling biological activities of neutrophils using midkine or its inhibitors. The present invention relates to agents for controlling neutrophilic functions comprising midkine or its inhibitor as an active ingredient. More specifically, this invention relates to (1) an agent for stimulating neutrophilic chemotaxis, comprising midkine as an active ingredient,
(2) the agent of (1), wherein the neutrophilic chemotaxis is based on haptotactic mechanism,
(3) an agent for treating a neutrophilic functional disorder, comprising midkine as an active ingredient,
(4) an agent for treating an inflammatory disease, comprising a midkine inhibitor as an active ingredient,
(5) the agent of (4), wherein the inflammatory disease is rheumatoid arthritis or osteoarthritis,
(6) the agent of (4), wherein the midkine inhibitor is an anti-midkine antibody, and
(7) the agent of (4), wherein the midkine inhibitor is a midkine antagonist.

As used herein, the "agents for treating neutrophilic functional disorders" include not only the agents for treating neutrophilic functional disorders but also agents for relieving unpleasant conditions of neutrophilic functional disorders. Similarly, the "agents for treating inflammatory diseases" used herein include not only the agents for treating inflammatory diseases but also agents for relieving unpleasant conditions of inflammatory diseases.

Agents containing midkine as an active ingredient of the present invention can stimulate neutrophilic chemotaxis. Chemotaxis means a process that leukocytes including neutrophils migrate to inflammatory sites (infected sites) along a concentration gradient of a chemotactant factor and accumulate there. After the migration, neutrophils adsorb microorganisms such as bacteria, uptake (phagocytosis), and eliminate them by various mechanisms. Chemotaxis is an important step for neutrophils to perform their own functions. There are two migration mechanisms, chemotactic mechanism and haptotactic mechanism. In the chemotactic mechanism, a chemotactant factor is a humoral factor that can diffuse from the place where it is produced, namely where its concentration is highest. Cells migrate toward the place where the chemotactant factor level is high. In contrast, in the haptotactic mechanism, a chemotactant factor attaches vascular endothelial cells or extracellular matrices, and cells migrate to the tissue with the highest density of the chemotactant factor. The present inventors demonstrated that midkine acts based on not the chemotactic mechanism but the haptotactic mechanism.

The agents of the present invention comprising midkine as an active ingredient can be used for treating neutrophilic functional disorders. Major neutrophilic functions are migratory, phagocytic, and microbicidal activities. Neutrophilic functional disorders are defined as a state in which one or more of these three activities are impaired. An example of neutrophilic functional disorders is lazy-leukocyte (chemotaxis-deficient leukocyte) syndrome that is a neurotaxis deficient disease. As described above, the present inventors have revealed that midkine stimulates neutrophilic migration, indicating that the impaired functions of neutrophils that are unable to migrate can be restored by acting midkine on them.

If desired, the agents of this invention for treating neutrophilic functional disorders can be used together with other factors which can enhance neutrophilic functions, including, for example, granulocyte colony-stimulating factor (G-CSF), granulocyte-macrophage colony-stimulating factor (GM-CSF), interleukin-8 (IL-8), macrophage colony-stimulating factor (M-CSF), and the like.

Midkine used in the present invention can be derived from any mammalian species including human (see, Examples in Unexamined Published Japanese Patent Application No. (JP-A) Hei 9-95454 and), mouse (Kadomatsu, K., et al., Biochem. Biophys. Res. Commun., 151: 1312-1318, 1988), rat, etc. Midkine used in the present invention includes intact midkine polypeptide, and its derivatives and homologues having midkine biological activities in which one or more amino acid residues of partial peptide sequences of the intact polypeptide are substituted or deleted. The midkine polypeptide of the present invention may be glycosylated or unglycosylated.

Agents containing a midkine inhibitor of the present invention as an active ingredient can be used for treating inflammatory diseases. The present inventors have demonstrated that midkine is present at high concentrations in inflammatory sites of patients with inflammatory diseases. Inflammation is closely associated with neutrophilic migration as is well known in the art. Accordingly, it is presumed that the suppressive effect of midkine inhibitors on neutrophilic motility can treat inflammatory diseases. Inflammatory diseases mean a disease with clinical manifestation of inflammation in any cases in which the disease results in or results from inflammation. Inflammation in higher animals is characteristically caused by a series of reactions in the microcirculation system in response to stimulation. In ordinary inflammation, microvessels transiently constrict, and then dilate, and the capillary bed, which is closed in an ordinary state of tissues, opens and increases blood supply. In addition, intracellular spaces between vascular endothelial cells in venular regions become wider and plasma components effuse therethrough to tissues (vasopermeability enhancement). The vasopermeability enhancement occurs in a biphasic fashion: the first-phase reaction is a weak reaction triggered by histamine or serotonin, which is called the immediate permeation; and the second-phase reaction is major vasopermeation in inflammation, which is called the delayed permeation. Polymorphonuclear leukocytes, monocytes (called macrophages after emigrating to tissues), lymphocytes, etc. emigrate through the venular region to tissues. Activators produced by these plasma components and cells enhance the proliferation of tissue cells and stimulate tissue restoration. This process is known to manifest as rubor, dolor, calor, and tumor. Inflammation, which is basically a local biological protective reaction, can also be tissue-toxic, and therefore functional impairment is recognized as one of main symptoms of inflammation. Inflammation reaction comprises dynamic processes of a complex reaction of alteration, circulatory disturbance, and proliferation of local tissues and cells. Inflammatory conditions are classified into three classes, alterative, exudative, and proliferative inflammations depending on the symptoms that strongly manifest. The conditions are also classified into acute and chronic inflammations with regard to the course of inflammation. Inflammation diseases include, for example, rheumatoid arthritis (RA) and osteoarthritis (OA).

Preferable examples of midkine inhibitors used in the present invention are an effective amount of heparin (Kaneda, N., et al., J. Biochem. 119:1150-1156, 1996) and human ryudocan that binds competitively to the binding site of midkine and inhibits the midkine activity (Kojima, T., Katsumi, A., Yamazaki, T., Muramatsu, T., Nagasaka, T., Ohsumi, K., and Saito, H., J. Biol. Chem. 271(10): 5914-5920, 1996). Anti-midkine antibody, among others, is most preferable. The antibody may be a polyclonal or monoclonal antibody.

Polyclonal antibody against midkine can be prepared as follows. A solution of recombinant human midkine prepared by an appropriate method is mixed with an equal volume of Freund's complete adjuvant (FCA) to obtain a homogeneous emulsion. The emulsion is injected subcutaneously at approximately 10 sites per a rabbit (New Zealand White, from 2,500 to 3,000 g). The injection sites are disinfected with cotton containing 70% ethanol. After this first immunization, Freund's incomplete adjuvant (FIA) is used as an adjuvant instead of FCA in the second and later immunization. Immunization is performed every two weeks. One week after the third immunization, blood is sampled from the rabbit, centrifuged at 1,600 rpm at 4° C. to obtain serum, which is examined for the titer of anti-midkine antibody. When the antibody titer is increased to a satisfactory level, then the entire blood is collected from the rabbit after the fourth or fifth immunization. Serum is obtained from the entire blood by centrifugation at 1,600 rpm at 4° C. as described above. The anti-midkine antibody is purified from the serum using protein A. The antibody is then further purified by affinity column chromatography using a human midkine polypeptide-bound column. Anti-midkine polyclonal antibody can be prepared through the procedures described above. Animals to be immunized are not limited to rabbits. Anti-midkine antibodies are obtained from various animal species immunized by essentially the same method as described above.

Monoclonal antibody against midkine can be prepared by the method reported by Kohler and Milstein (Kohler, G. and Milstein, C., Nature 256: 495-497, 1975).

Anti-midkine antibodies include humanized antibodies (Noguchi, H., and Azuma, T., Preparation of chimera antibodies by antibody engineering and its application, Medical Immunol. 22: 628-638, 1991; Noguchi, H., Rationale and clinical application of chimeric antibodies and humanized antibodies, Igakunoayumi 167: 457-462, 1993; and Nakatani, T., and Noguchi, H., Humanization of antibodies, Pharmacia 33: 24-28, 1997), human antibodies (Chothia, C. et al., Nature, 324: 877, 1989; Roguska, M. L., et al., Proc. Natl. Acad. Sci. U.S.A., 91: 969, 1994; Winter, G. et al., Annu. Rev. Immunol., 12: 433, 1994; and Lonberg, N, et al., Nature, 368: 856, 1994), chimeric antibodies (Morrison, S. L. et al., Proc. Natl. Acad. Sci. U.S.A., 81: 6851, 1984; and Noguchi, H., and Azuma, T., Medical Immunology, 22: 628-638, 1991), etc.

Midkine polypeptide used as an antigen for antibody preparation may be any midkine polypeptides derived from mammalian species including human (JP-A-Hei 6-217778), mouse (Kadomatsu, K. et al., Biochem. Biophys. Res. Commun., 151: 1312-1318, 1988), rat, etc. Partial peptides derived from intact midkine and having biological activities of midkine can be used as an antigen for preparing anti-midkine antibody. Derivatives or homologues of midkine or its partial peptide, in which one or more amino acids are substituted or deleted, can also be used. Midkine polypeptide used as an antigen may be glycosylated or unglycosylated.

A midkine antagonist can be prepared by, for example, determining an amino acid sequence of midkine that is crucial for activating neutrophilic functions, and deleting the sequence.

The agents of the present invention comprising midkine or its inhibitor as an active ingredient can be given to patients for stimulating chemotaxis of neutrophils, for treating neutrophilic functional disorders, or for treating inflammatory diseases. The dose of the active ingredient may vary depending on sex, body weight, and conditions of patients. In general, it can be administered to a patient in a daily dose of from 0.1 to 1000 mg once or several times. Preferably, midkine or its inhibitor can be formulated into an aqueous solution or in an appropriate dosage form together with pharmaceutically acceptable carries and administered intravenously, subcutaneously or intramuscularly.

BEST MODE FOR CARRYING OUT THE INVENTION

Examples of the present invention are described below, but. are not construed to limit the scope of this invention.

EXAMPLE 1

Detection of Midkine (MK) by ELISA

Figure 1:
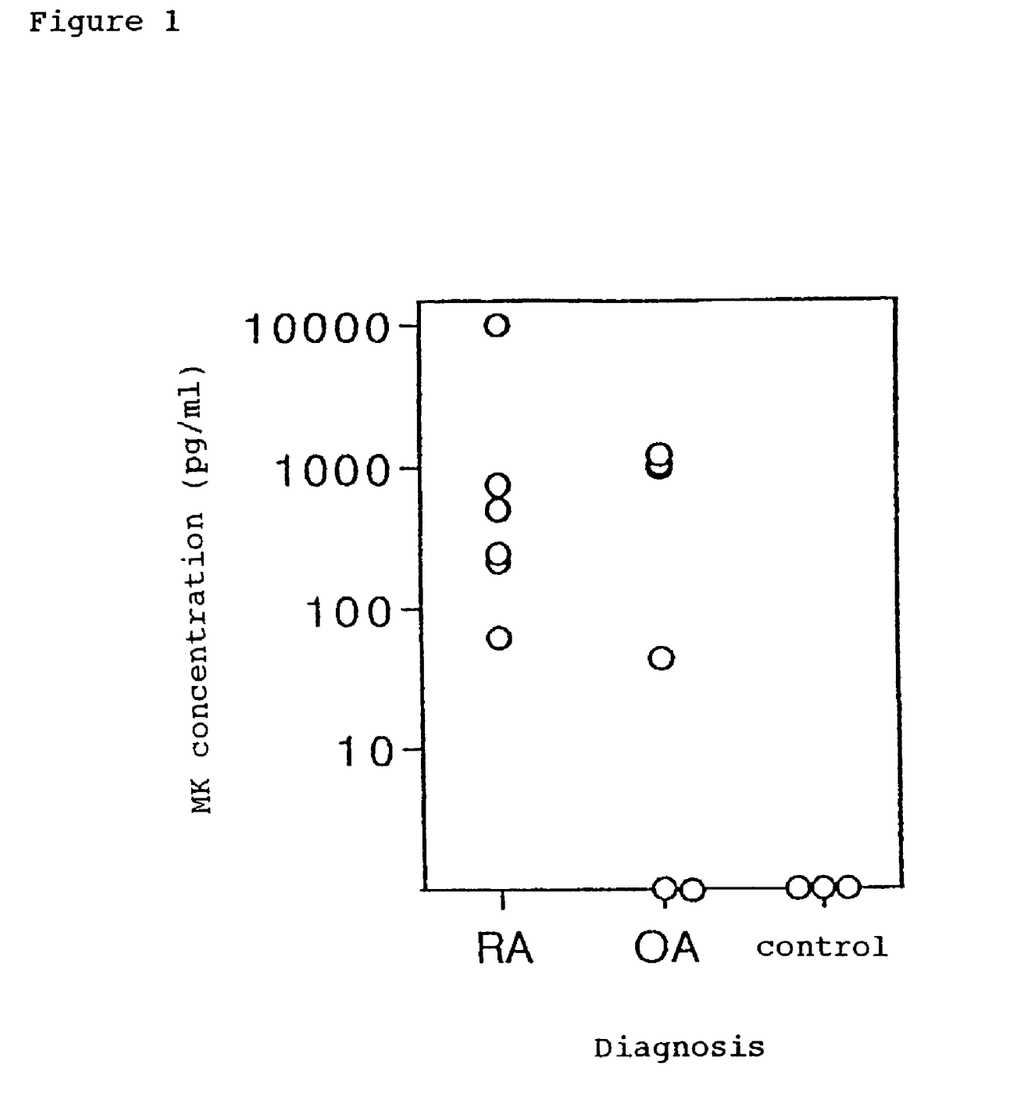
FIG. 1 is a graph showing a result of enzyme-immunoassay for MK polypeptide in synovial fluid. The detection limit was 9 pg/ml in this assay. The MK concentrations below the detection limit are plotted on the base line of the abscissa.

Samples of synovial fluid were collected by aspiration from patients (aged 26 to 72; average age 52 years) with inflammatory synovitis of OA or RA. Mk in the sample of synovial fluid was assayed by ELISA (Muramatsu, H. et al., J. Biochem. 119: 1171-1175, 1996). MK was not detected in any synovial fluid samples derived from the three healthy subjects, while MK was detected in all the samples derived from six patients with RA (FIG. 1; 62 to 10,000 pg/ml of the MK concentration). A significant amount of MK was also detected in four out of six samples each derived from different OA patients (FIG. 1; below the detection limit to 1225 pg/ml). The results indicate that MK levels in synovial fluid correlate significantly with inflammatory states in synovitis.

EXAMPLE 2

Immunohistochemical Detection of MK

Synovial tissues were obtained from the entire knee parts of three RA patients and two OA patients. All the biopsy samples contained hyperplastic inflammatory periosteum tissues which are characterized histologically by propagation of lining cells of the synovial membrane, extensive infiltration of lymphocytes and macrophages, and vigorous angiogenesis. Immunohistochemical examination was carried out using the method of Muramatsu et al. (Muramatsu, H., et al., Dev. Biol. 159: 392-402, 1993). The biopsy samples were fixed with neutrally buffered formalin, embedded in paraffin, and sliced into sections with 5-μm thickness. The sections were incubated with anti-human MK antibody (15 mg/ml) in PBS containing 0.2% bovine serum albumin and 2% normal goat serum at 4° C. overnight. The anti-human MK antibody was prepared by the method of Muramatsu et al. (Muramatsu, H., et al., J. Biochem. 119: 1171-1175, 1996) using a rabbit immunized with chemically synthesized human MK purchased from Peptide Institute, Inc. Control sections were incubated with PBS containing 2% bovine serum albumin or normal rabbit serum. The sample and control sections were incubated with biotinylated goat anti-rabbit antibody (diluted to antibody:PBS=1:250) and washed. The sections were then incubated with an avidin-biotin peroxidase conjugate (Vector Laboratories Inc., Burlingame, U.S.A.), followed by adding 3-amino-9-ethylcarbazole (AEC) containing 1% hydrogen peroxide and incubating the mixture to develop color.

Figure 2:
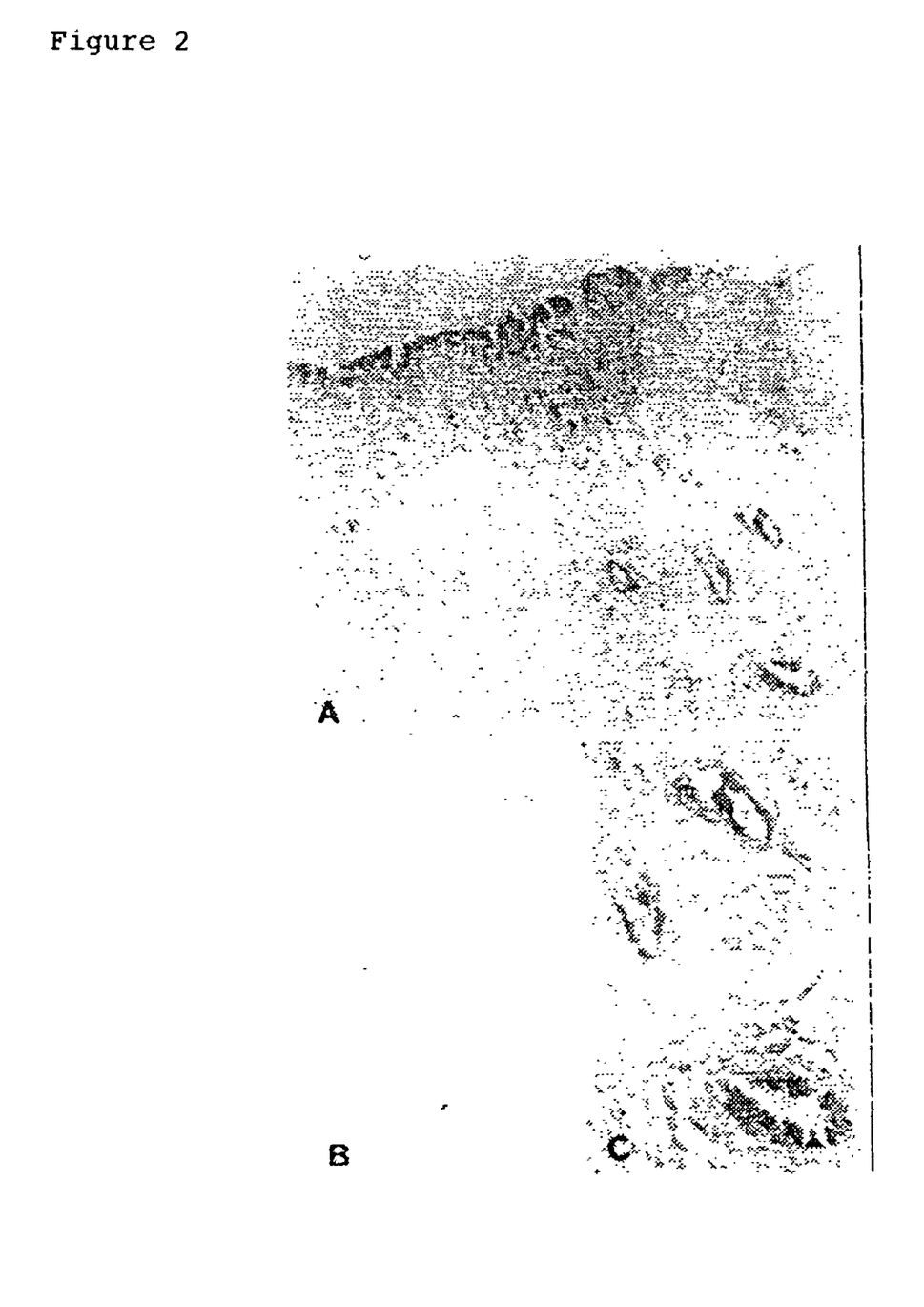
FIG. 2 depicts microphotographs of immunohistochemically stained inflammatory synovial tissue sections derived from a patient with active inflammation of rheumatoid arthritis (RA) in synovial fluid. Panel A indicates a stained section between synovial cells and a neogenetic vessel; B stained synovial parietal cells, and C stained vascular endothelial cells of a neogenetic vessel. Magnification was 104 fold in panel A; 208 fold in panels B and C.

Using anti-MK antibody, the samples from two patients with RA were stained broadly in a region between the synovial parietal cells and neogenetic vessels (FIG. 2A). Interestingly, the synovial parietal cells (FIG. 2B) and the capillary endothelial cells (FIG. 2C) were strongly stained by MK. The sample from one RA patient was not strongly stained as compared with samples from the other patients. This can be explained that the states of the conditions were not active in this patient. The degree of immunological staining of two cases of OA with the inflammatory synovial with the anti-MK antibody was comparable to the inflammatory synovial membrane of RA patients. Samples of the synovial membrane from healthy subjects were not available. Instead the biopsy samples free of inflammatory synovial membrane from patients who underwent artificial joint replacement were examined. These samples were not immunologically stained.

EXAMPLE 3

Detection of MK by Western Blot Analysis

Figure 3:
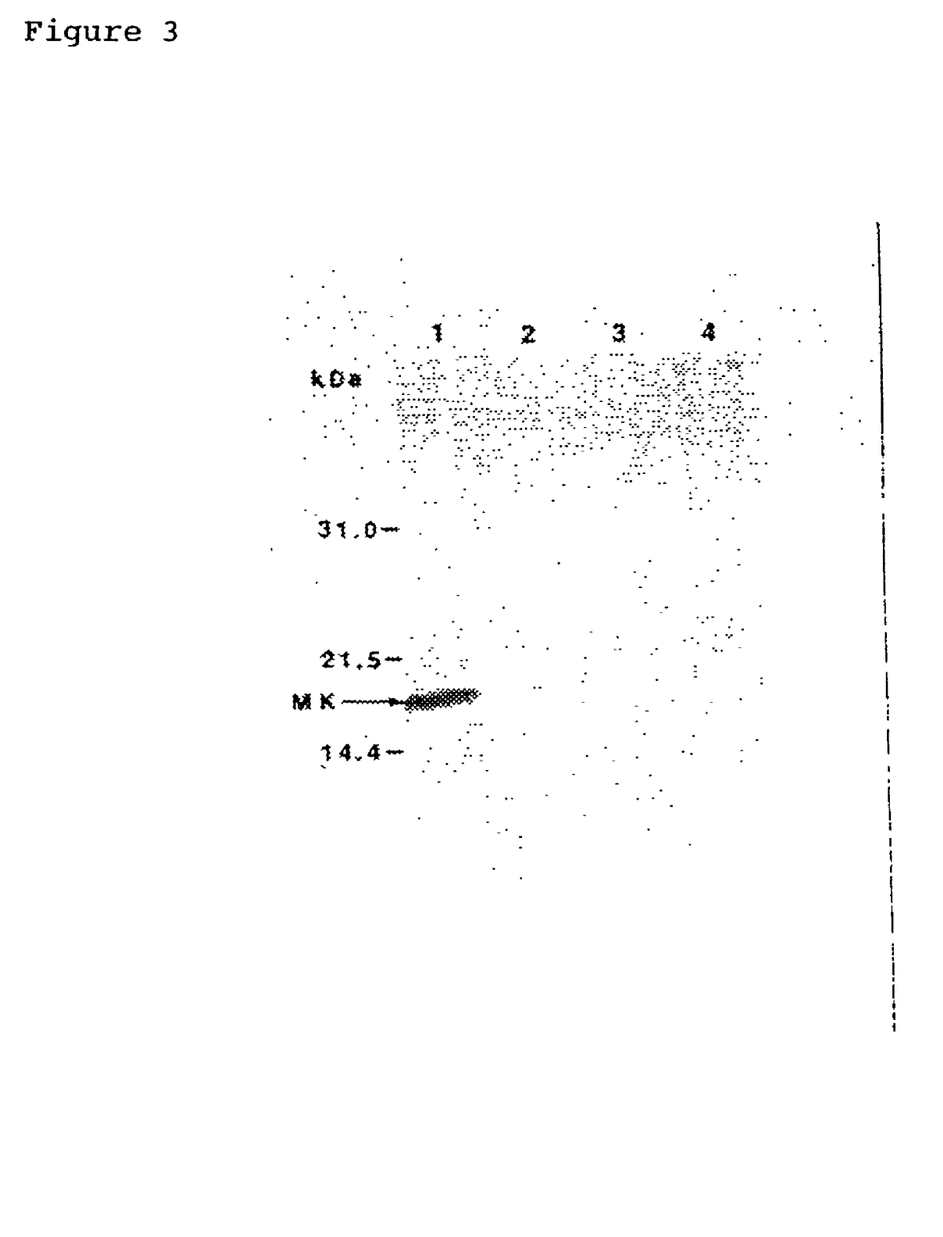
FIG. 3 is a photograph showing a pattern of Western blot analysis of extracts from synovial tissues. Lane 1 is for the tissue with active synovitis of an OA patient; lane 2, the tissue with active synovitis of an RA patient; lane 3, the tissue of inactive synovitis; and lane 4, the synovial tissue with no histologically severe inflammation derived from a patient who underwent artificial joint replacement.

The synovial tissue extract was subjected to Western blot analysis. The samples were electrophoresed in an SDS-polyacrylamide gel by the method of Laemmli (Laemmli, U. K., Nature 227: 680-685, 1970), and proteins in the gel were transferred onto a nitrocellulose membrane by the method of Towin et al. (Towin, H. et al., Proc. Natl. Acad. Sci. USA. 76: 4350-4354, 1979). The nitrocellulose membrane was incubated in Dulbecco's phosphate-buffered saline (PBS) containing 5% skim milk at 4° C. overnight, and then incubated with diluted anti-human MK antibody (diluted to 20 mg/ml with a 5% skim milk solution) at room temperature for 2 hours. The nitrocellulose membrane was then washed with PBS containing 0.1% Tween 20, incubated with affinity-purified anti-rabbit IgG-horseradish peroxidase conjugate (Jackson Immunoresearch Laboratories, Inc. Baltimore, USA), and stained with 4-chloro-1-naphthol. MK was detected at a high level in the extract of active inflammatory synovial membrane from an OA patient (FIG. 3, lane 1). While the inflammatory site of active sinovitis in an RA patient contained MK at a moderate level (FIG. 3, lane 2), the MK level was low at a non-active inflammation site of the same patient (FIG. 3, lane 3). MK was not detected in samples derived from patients who underwent artificial joint replacement and patients who were not affected with inflammatory synovitis (FIG. 3, lane 4). The immunoreactive substance was thus confirmed to be MK. Furthermore, the correlation of the expression level of MK with the severity of inflammation, which had been found by immunohistochemistry, was also identified by Western blot analysis.

EXAMPLE 4

Effect of MK on Migration of Human Neutrophils

Figure 4:
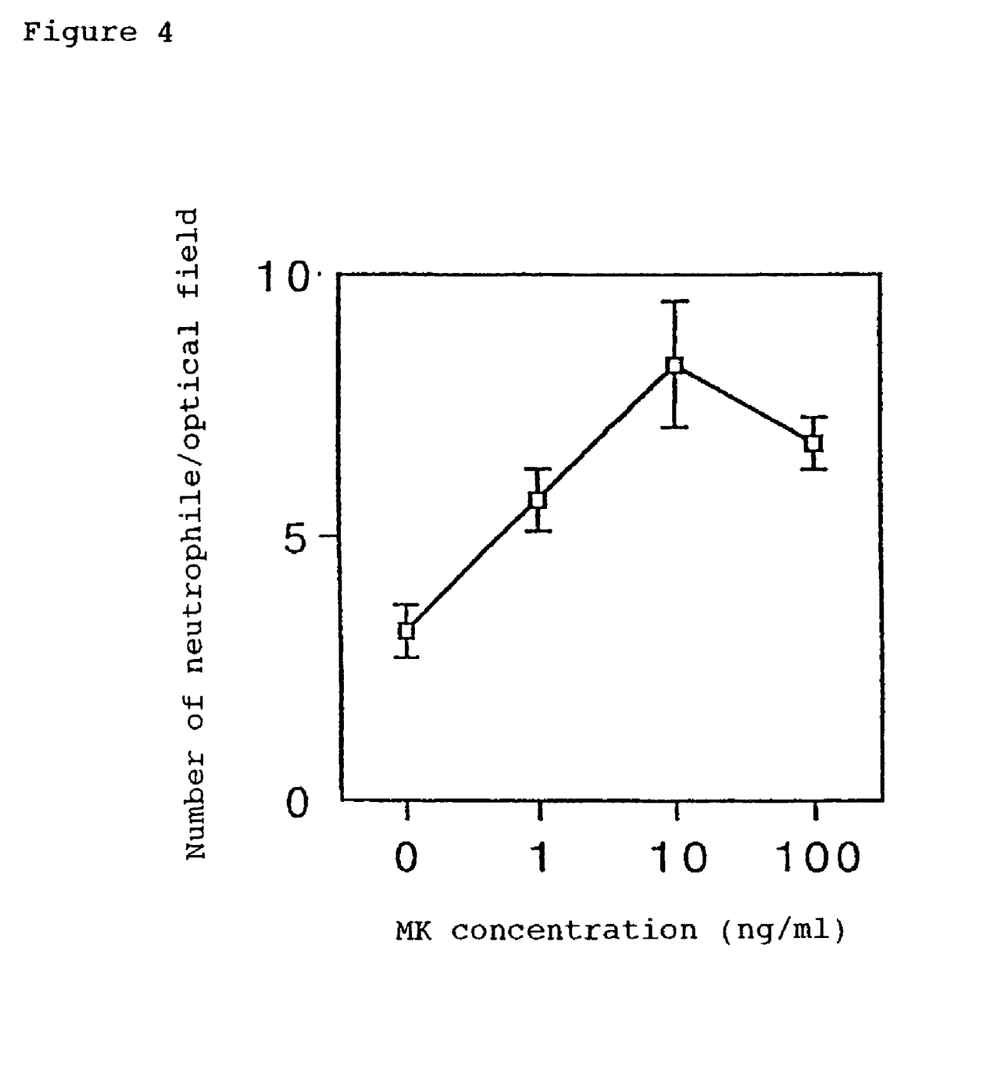
FIG. 4 is a graph showing the degree of neutrophilic migration in response to MK. MK was added into bottom wells at a predetermined concentration. After a 3-hour incubation in the presence of MK, the number of neutrophils migrated to the lower surface of the filter was counted. The average number of neutrophils migrated per optical field was plotted against the MK concentration.

Chemotaxis of neutrophils induced by MK was assayed in order to evaluate the role of MK in leukocyte mobilization at earlier stages of the inflammation reaction. Neutrophils were separated from peripheral blood of healthy subjects by specific gravity centrifugation in Ficoll-Hypaque (Venaille, T. J. et al., Scand. J. Clin. Lab. Invest. 54: 385-391, 1994). The collected cells were rinsed with PRMI1640 culture medium and suspended in the same medium supplemented with 10% human serum with the blood type AB to a cell concentration of $2.5 \times 10^6$ cells/ml. Neutrophilic migration induced by MK was measured with Chemotaxicell (Kurabo Co., Ltd., Osaka, Japan), which was used as a top chamber. Chemotaxicell is identical to the Boyden chamber equipped with a polycarbonate filter. A 24-well culture plate (3047, Falcon) was used as a bottom chamber. MK diluted with RPMI1640 culture medium supplemented with 10% human serum with the blood type AB were added to wells of the 24-well plate. Subsequently, neutrophils ($5 \times 10^5$ cells) suspended in the same culture medium were placed in Chemotaxicell. The chamber was incubated in a 5% $CO_2$ incubator in a humid atmosphere at 37° C. for 3 hours. The cells migrated through the filter with 5-μm pores were fixed with 100% ethanol, stained, and then counted under a microscope (Olympus AX80, 400 magnifications). In each assay netrophils were counted in 10 optical fields. Each sample was assayed in triplicate. The data were represented as average number±standard deviation. This experiment revealed that MK in the bottom chamber stimulates the migration of neutrophils in the top chamber (FIG. 4). The optimal concentration of MK to induce neutrophilic migration was 10 ng/ml (level of significance: $p<0.01$) (FIG. 4).

Figure 5:
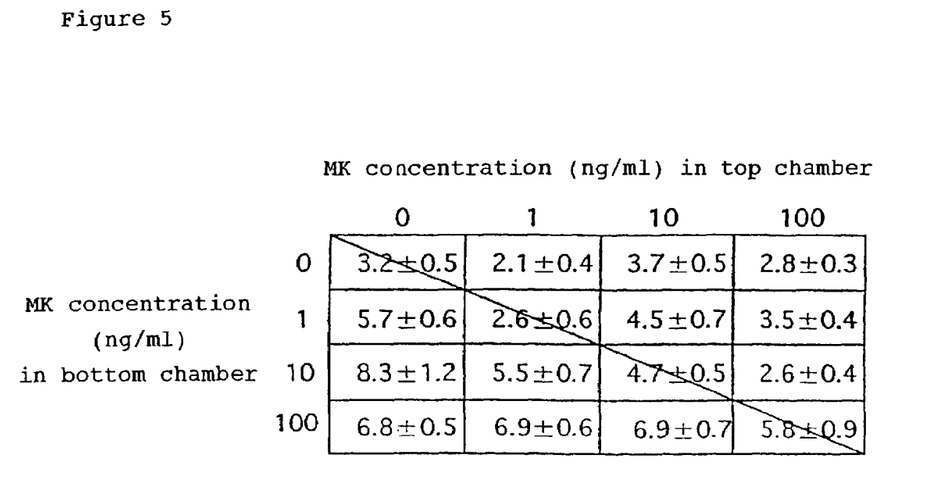
FIG. 5 shows a result of checkerboard analysis for neutrophilic migration stimulated by MK. Data are represented as an average number of neutrophils migrated per optical field ±standard deviation (n=4). The data on the crossed line are average values of the cell number per optical field in the absence of MK concentration gradient.

Checkerboard analysis (Zigmond, S. H., and Hirsch, J. G., J. Exp. Med. 137:387-410, 1973) was performed to clarify whether the MK-dependent neutrophilic migration is governed by an oriented movement with recognizing the concentration gradient of the chemotactant factor (chemotaxis), or by a random movement (chemical motility). The result is illustrated in FIG. 5.

It is obvious from the data shown in the figure that an increased number of neutrophils migrates through the filter when the MK concentration gradient is made in such a manner that the MK concentration is higher at the bottom chamber and lower at the top chamber, indicating that MK functions as a chemotactant factor.

EXAMPLE 5

Mechanism of MK-dependent Chemotaxis

Acquisition of the motility of cells is recognized as an adhesion-dependent event (Timothy, A. S., Cell 76: 301-314, 1994). MK binds strongly to syndecan (Mitsiadis, T. A. et al., Development 121: 37-51, 1995; and Kojima, T. et al., J. Biol. Chem. 271(10): 5914-5920, 1996) that belongs to the family of cell surface heparan sulfate proteoglycan (Elenius, K. et al., J. Cell. Biol. 114: 585-595, 1991). The ability of matrix-bound MK to enhance the neutrophilic migration was examined. Specifically, the assay for the haptotactic mechanism was carried out by the method of Rot (Rot, A., Eur. J. Immunol. 23: 303-306, 1993) to determine whether MK functions in the free form (chemotactic mechanism) or in the matrix-bound form (haptotactic mechanism).

As the initial step in the assay for the haptotactic mechanism, the lower surface of the filter was pre-coated with MK by adding MK (1 to 100 ng/ml) in the bottom wells, and the corresponding top wells were filled with RPMI1640 medium to establish positive haptotactic gradients of MK.

In another set for the negative control assay, the upper surface of the filter were pre-coated with MK by adding MK (1 to 100 ng/ml) in the top wells, the corresponding bottom wells were filled with RPMI1640 medium, thereby establishing negative haptotactic gradients.

In the assay for the chemotactic mechanism, both top and bottom wells were filled with RPMI1640 medium (chemotactic gradients).

Each well was incubated at 37° C. for 20 minutes, and the Chemotaxicell composed of the top chamber and the polycarbonate filter was washed well with RPMI solution to remove unbound (free) MK molecules.

As the second step, both top and bottom wells were filled with RPMI solution containing 10% serum with the blood type AB in the assays for the haptotactic mechanism and the negative control. In the assay for the chemotactic mechanism, MK (1 to 100 ng/ml) was added to the bottom chamber.

Neutrophils ($5\times10^5$) were placed in the top wells in each set prepared in the second step. The wells were incubated at 37° C. for 30 minutes, and the motility of neutrophils was measured by counting the neutrophils migrated through the filter. In each assay neutrophils were counted in 10 optical fields. Each sample was assayed in triplicate. The data were represented as the number of the migrated cells±standard deviation.

Figure 6:
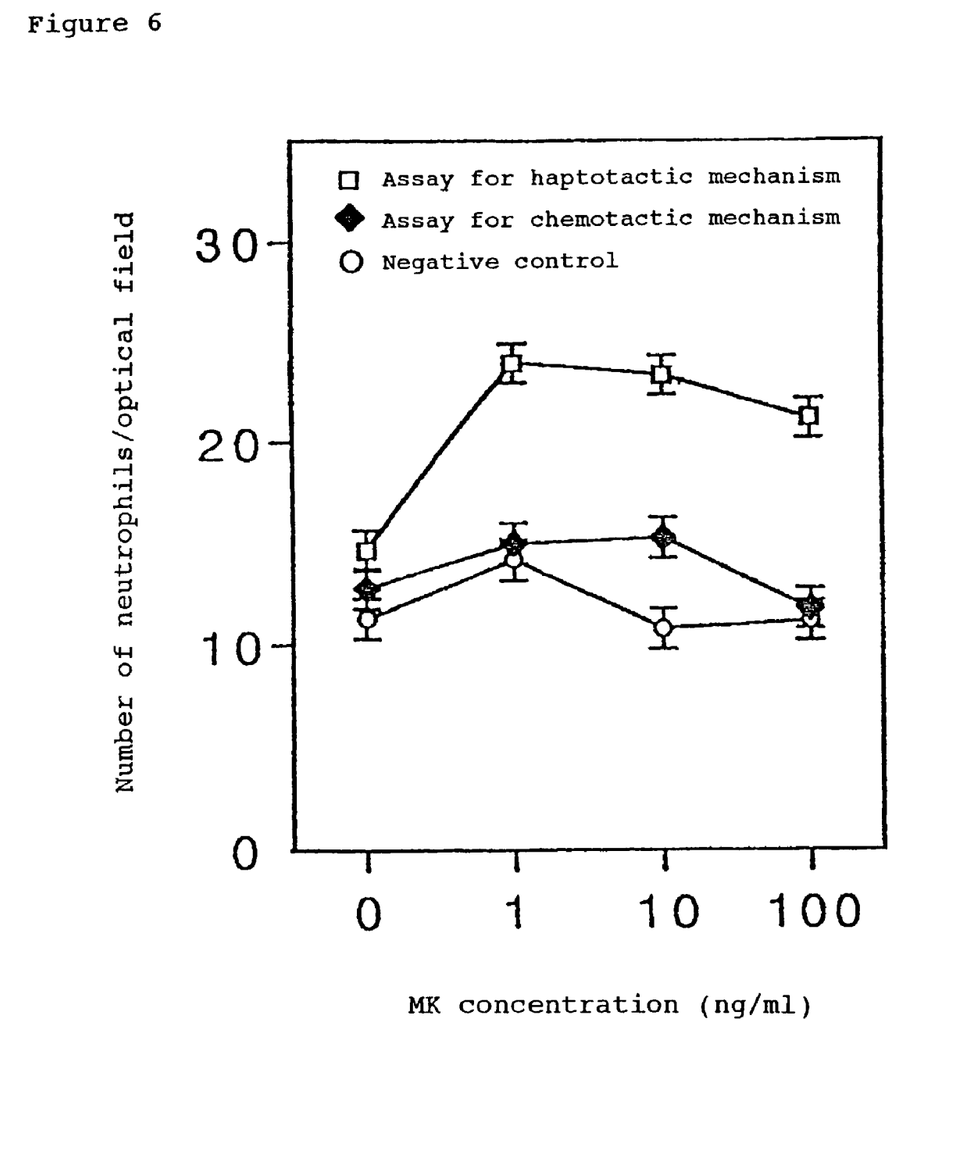
FIG. 6 is a graph showing the degree of MK-dependent migration of neutrophils based on haptotactic or chemotactic mechanism plotted against the MK concentration. Open squares present the result of assay for the haptotactic mechanism in which MK was pre-coated on the lower surface of the filter; filled diamonds the result of assay for the chemotactic mechanism in which MK was pre-coated on both surfaces of the filter; open circles the results of negative control in which MK was pre-coated on the upper surface of the filter. After 30-minute incubation, the number of neutrophils migrated to the lower surface of the filter was counted. A value plotted represents a mean value of the migrated cell number per optical field.

In the assay for the haptotactic mechanism, the filter-bound MK stimulated neutrophilic migration even at a low concentration of MK (1 ng/ml; level of significance, $p<0.01$) during the short period (30 minutes) of incubation (FIG. 6, open squares). In contrast, the neutrophilic migration was not stimulated after a 30-minute incubation in the assay for the chemotactic mechanism (FIG. 6, filled diamonds) as well as in the negative control assay (FIG. 6, open circles). These results indicate that the midkine-stimulated neutrophilic migration was based on the haptotactic mechanism.

INDUSTRIAL APPLICABILITY

The present invention provides novel agents for controlling neutrophilic functions comprising midkine or its inhibitor as an active ingredient. The invention enables treatment of neutrophilic functional disorders by stimulating neutrophilic migration or treatment of inflammatory diseases by inhibiting neutrophilic migration.

We claim:

1. A method for inhibiting a neutrophilic function, wherein the inhibition is achieved by administering to a subject in need thereof, an effective amount of an inhibitor of mammalian midkine, wherein said inhibitor of mammalian midkine is an anti-midkine antibody.

2. The method of claim 1, wherein the neutrophilic function is migration.

3. The method of claim 2, wherein the migration is based on chemotaxis.

4. A method for treating or relieving an inflammatory disease in which midkine levels are elevated, wherein the method is achieved by inhibiting neutrophilic functions, wherein the inhibition is achieved by administering to a subject in need thereof, an effective amount of an inhibitor of mammalian midkine, wherein said inhibitor of mammalian midkine is an anti-midkine antibody.

5. The method of claim 4, wherein the inflammatory disease is rheumatoid arthritis or osteoarthritis.

6. The method of claim 1, wherein the anti-midkine antibody is a polyclonal antibody.

7. The method of claim 1, wherein the anti-midkine antibody is a monoclonal antibody.

8. The method of claim 1, wherein the anti-midkine antibody is a humanized antibody.

9. The method of claim 1, wherein the anti-midkine antibody is a chimeric antibody.

10. The method of claim 1, wherein the anti-midkine antibody is an anti-human midkine antibody.

11. The method of claim 4, wherein the anti-midkine antibody is a polyclonal antibody.

12. The method of claim 4, wherein the anti-midkine antibody is a monoclonal antibody.

13. The method of claim 4, wherein the anti-midkine antibody is a humanized antibody.

14. The method of claim 4 wherein the anti-midkine antibody is a chimeric antibody.

15. The method of claim 4, wherein the anti-midkine antibody is an anti-human midkine antibody.

* * * * *